United States Patent [19]

Jost

[11] Patent Number: 5,434,045
[45] Date of Patent: Jul. 18, 1995

[54] BIOLOGICAL SUPPORT SYSTEM CONTAINER

[76] Inventor: Leonora I. Jost, 21 Rosewood Cir., Unit 1, Kennebunk, Me. 04043

[21] Appl. No.: 883,896

[22] Filed: May 8, 1992

Related U.S. Application Data

[63] Continuation of Ser. No. 385,368, Jul. 27, 1989, abandoned.

[51] Int. Cl.⁶ .......................... C12M 1/00; F25D 3/10; F25D 31/00
[52] U.S. Cl. ........................................ 435/1; 435/260; 435/283; 435/287; 435/289; 435/290; 435/313; 62/64; 62/440; 62/457.1; 220/4.01; 220/4.06; 220/4.21; 220/4.22; 220/4.32
[58] Field of Search .................. 435/1, 260, 283, 284, 435/287, 289, 290, 296, 313; 62/64, 78, 440, 457.1, 457.9, 451; 220/4.21, 4.22, 4.32, 4.01, 4.06

[56] References Cited

U.S. PATENT DOCUMENTS

| | | | |
|---|---|---|---|
| 1,950,781 | 3/1934 | Burns | 62/457.9 |
| 3,406,531 | 10/1968 | Swenson et al. | 62/306 |
| 3,810,367 | 5/1974 | Peterson | 62/457 |
| 3,881,990 | 5/1975 | Burton et al. | 195/1.7 |
| 4,042,142 | 8/1977 | Ruano | 220/4.21 |
| 4,086,784 | 5/1978 | Wagner | 62/374 |
| 4,473,552 | 9/1984 | Jost | 424/101 |
| 4,745,759 | 5/1988 | Bauer et al. | 62/3 |
| 4,997,521 | 3/1991 | Howe et al. | 156/651 |
| 5,104,808 | 4/1992 | Laska | 435/7.92 |

FOREIGN PATENT DOCUMENTS 0256730  2/1988  European Pat. Off. .

*Primary Examiner*—William H. Beisner
*Assistant Examiner*—Jane Williams
*Attorney, Agent, or Firm*—The M. H. Sears Law Firm Chartered

[57] ABSTRACT

A unique method of obtaining a recycling of air and/or plasmas, to allow a controlled system for creating and regulating temperature in a container facilitating transport and long-term storage of biological matter. This method allows a sterile packaging of donor biological matter, in protective solutions of extracellular agents, in a controlled temperature system which is regulated by air and/or inert gas refrigerants, passing over a micromotor, the RPM's of which will set the speed of the refrigerants that regulate the temperature of the contained biological matter. It is comprised of an inert plastic or latex top member which holds the mechanical system, which is placed into the molded plastic based member, which holds a sealed well for placing the donor collected biological matter.

20 Claims, 3 Drawing Sheets

BIOLOGICAL SUPPORT SYSTEM CONTAINER

This application is a continuation of application Ser. No. 385,368, filed Jul. 27, 1989 now abandoned.

BACKGROUND OF THE INVENTION

The failure of mammalian tissue to carry out its expected metabolic functions can occur as a result of known causes such as e.g., disease, congenital defect, natural causes, etc. The ability to surgically excise malfunctioning or biologically deceased tissue and subsequently replace the removed tissue with comparable replacement tissue from a tissue donor has been known in the medical field for many years. Similarly, various processes of transfusing healthy whole blood, collected from willing donors for placement into recipients whose blood supply has been naturally or artificially depleted, due either to a trauma related accident or disease, have been recognized in the medical field.

Biological tissues, including organs and whole blood, or its separate component fractions, hereinafter referred to collectively as biological matter, cannot survive outside of their natural environment without some form of storage or preservation.

Biological degradation of the removed biological matter begins almost immediately while awaiting implantation or introduction into a recipient, as the excised matter is subjected to new environments possessing varied concentrations of familiar and foreign gases and liquids. In an attempt to minimize such degradation due to the altering of the biological matter's delicate metabolic balance, many theories, to date, have been advanced. However, none of the existing technology resulting from these preservation theories has provided a satisfactory solution to the problem of "long-term" biological matter preservation. It should be understood that "long-term" storage or preservation in this field translates into preservation of the 1) living biological tissue and 2) whole blood, without significant biodegradation or other loss of its natural functional capability, for a period of time no less than ten days and sixty days respectively.

Early attempts to preserve excised tissue used some form of cryogenic treatment whereby the biological tissue or organ was frozen, then thawed. The problems of crystal formation, and molecular expansion causing cell rupture prompted investigators to first drain the excised tissue of its natural fluids and replace them with a plasma-like perfusate designed to behave as an "antifreeze" within the organ or tissue. Significant problems remained, however, with respect to the perfusate. Many perfusates caused allergic reactions in the recipient and often led to the outright refusal of the organ tissue by the recipient's immune system.

The often encountered need to transport biological matter, in a preserved form, has led to further complications. Recipients, who are often in a weakened condition themselves, must hurriedly travel to the site of the excised organ, or, as is the usual case, the biological matter must be shipped to the site of the recipient.

There are currently available so-called "portable" biological transportation devices that maintain the metabolic function of the biological matter in transit, by either freezing the organ/tissue; i.e. bringing the temperature of the organ/tissue to 0° C., or flowing a simulated plasma or perfusate through the organ, often at a low temperature, but above the freezing point. These transportation methods have met with reasonable success. However, the necessary time frame involved from organ/tissue excision to actual transplantation remains extremely short; usually an organ can be artificially preserved ex vivo for only 24-72 hours. As a result, recipients domiciled in outlying geographic areas often suffer the additional financial hardship of extensive travel, on short notice, to receive a transplant. In many instances, potential recipients are determined by the geographic location of the donor, making transplant operations a practical impossibility for many individuals in need of such treatment.

As stated in my earlier U.S. Pat. No. 4,473,552, there is also a need to preserve and transport mammalian whole blood in a process that does not require the damaging freezing step for such preservation. Simple refrigeration which only maintains blood in a usable condition for 21 days, is also unsatisfactory. Therefore, there is a need for a suitable container or support system to preserve blood at refrigeration temperatures in a suitable transportable container for a duration exceeding 60-days.

The known methods of living biological tissue preservation and transportation require either freezing the tissue after a pretreatment with a suitable perfusate to retard the otherwise damaging effects of the low temperatures required, or, continuously pumping a liquid or gaseous perfusate through the tissue to nourish it at temperatures above that of freezing. Various containers, some of which are conceivably transportable, have been devised to carry out these tissue preservation methods.

One early device, described by Peterson in U.S. Pat. No. 3,810,367, comprised a container designed to have a human organ placed in a sterile saline solution in one compartment, and kept at 0° C. by a separate underlying ice-containing compartment. The organ compartment contained a removable liner comprised of materials inert to animal tissue. Toledo-Pereyra in U.S. Pat. No. 4,502,295 proposed another hypothermic organ storage unit that reduced the metabolic rate of the excised organs to be stored by maintaining the surrounding temperature within the storage receptacles from between 0° to 7° C. Ice was disclosed as the chilling means. The presence of a draining means, through which melted ice water could be removed, represented an improvement in the field. A further ice-cooled organ preservation device was described by Toledo-Pereyra in U.S. Pat. No. 4,242,883. This device also used ice to chill the container holding the organ awaiting transplantation (liver), as well as the perfusate being pumped through the organ. The device allegedly preserved the organ ex vivo for 24 hours. Bauer et al., in U.S. Pat. No. 4,745,759 describes a portable organ storage unit comprised of a thermoelectric (AC/DC) refrigeration system designed to maintain the temperature of the perfusate solution pumped through the stored organ at 4° C.

Chilled gases have also been used as a refrigeration means in connection with organ storage devices. Toledo-Pereyra, in U.S. Pat. No. 4,471,629, proposed the use of chilled helium perfused into a kidney while the organ was subjected to a pressurized nitrogen environment. In this patent, the organ is frozen to a temperature between −70° and −140° C. A thawing format using microwaves is suggested. The disclosure of de Roissart, in U.S. Pat. No. 3,607,646 contemplates the use of an inert gas environment to surround an excised organ awaiting transplantation while simultaneously reducing the amount of excess oxygen from the perfusion fluid. Exposure of the organ to amounts of oxygen in the perfusion fluid of more than 10 percent is disclosed as having adverse effects on the organ's preservation. Kraushaar, in U.S. Pat. No. 4,008,754 teaches the use of an inert gas, both to fill the organ to be preserved, and as its surrounding atmosphere, prior to freezing the organ to temperatures below $-100°$ C. As is well known, any device which employs temperatures below 0° C. is of little practical value for biological matter preservation because significant deterioration of the matter sought to be preserved is known to occur as a result of the freeze/thaw cycle.

The present invention provides a wider range of significant advantages over the prior art devices and methods for living biological matter preservation. It is applicable to the preservation of mammalian organs and other living biological tissue, as well as whole blood, or any component of such that contains or comprises living cells. The present device further uses a pneumatically powered micro-motor to recirculate a compressed air or pressurized inert refrigerant. This lowers the temperature of the chamber, or concave receptacle well containing the biological matter, to 1°–3° C. (or 34°–37° F.), thus eliminating the need for the elaborate thawing protocol made necessary when temperatures reach or drop below the freezing point. The use of a air, or recirculated inert gas refrigerant assures that the biological contents are cooled evenly, thus eliminating the danger of unequal temperature gradients within a preservation container. Such temperature differentiation can damage the living biological matter being preserved. When ice is used as the cooling agent, even the use of the best thermal conductive materials for the containers may allow a temperature gradient to exist within the container which endangers the viability of the preserved biological matter.

The presence and amount of available oxygen contained in the device is closely monitored by use of a sensor and readout means. A preferred preservative is hydroxyethyl starch (HES) or any preservative solution that will block and form a barrier surrounding healthy cells. The preservative completely surrounds the biological matter and fills the receptacle well thereby further inhibiting excess oxygen/biological matter interaction.

The entire device is transportable. The micro-motor is powered by pneumatic bursts of circulated air or inert gas. The bursts are triggered by integrated instrumentation powered by a rechargeable battery pack. The device can also be used for stationary storage and have its micro-motor powered by pneumatic pressure supplied by the introduction of additional pressurized inert gases such as e.g., nitrogen, into the container via injection ports. The method of use and operation of the device is simple and inexpensive. The living biological matter stored in this invention can be preserved at ordinary refrigeration temperatures for extended periods of time, far greater in duration than contemplated in the prior art. Whole blood may be kept indefinitely according to the procedures disclosed herein, and other biological tissue including organs or living cells may be maintained in transplantable condition for a minimum of ten days. The metabolic processes of the stored living biological matter are, in effect, drastically lowered during preservation, and are restored in viable, usable form and returned to a body temperature of 98.6° F.

SUMMARY OF THE INVENTION

The invention disclosed, broadly pertains to storage receptacles or chambers for transportable biological matter preservation and storage receptacles or chambers. Such a receptacle is comprised of a two-part construction. The lower part consists of the chamber or well containing either a sterile solution or a preserving gel into which is placed the organ or other biological matter to be preserved. An open-and-close plastic lid, molded into and being the top part of the well covers the chamber, and the upper portion of the device fits over, and locks onto the lower portion by a circumferentially threaded means extending around the upper portion and fitting into the lower portion. A stainless steel retaining rim, with a pressure lock, fits over the upper portion, locking it to the lower portion.

The two portions are designed and molded to create an empty airflow chamber which extends around the biological matter well, such that an even unidirectional airflow can be created around the well containing the biological matter. The biological matter is preserved in a preserving medium, maintained at refrigeration temperatures of from 1° to 3° C. The chilling agent is a pressurized air or inert gas introduced initially through gas injection ports located in the upper portion of the base member of the device, and circulated continuously through a sealed outer chamber surrounding an inner concave receptacle well, into which the biological matter to be preserved is placed. The inert gas coolant is continuously circulated by means of a micro-motor made of a low friction, low mass material, such as silicon, which may be operated in its stationary mode via pneumatic pressure when the device is connected to a pressurized inert gas source. When the unit is being transported, a rechargeable battery unit maintains proper coolant circulation by triggering a pneumatic burst of air or inert gas to the micromotor such that the desired motor speed is maintained. The battery also powers the oxygen sensors and readout means as well as any supplemental sensory instrumentation.

The concentration of available oxygen allowed in the empty outer air flow chamber is restricted to levels equalling between $\frac{1}{4}$ to 4% oxygen by volume based on the total volume contained in the airflow chamber and is closely monitored through the use of an oxygen sensor and readout means. Such careful regulation of the oxygen level is crucial to the sustained performance of the micro-motor which is extremely sensitive to any density changes in the gas mixture circulating in the airflow chamber. Allowing concentrations of oxygen to vary outside of the stated limits will cause the temperature of the biological contents contained within to leave the critical range of 34°–37° F. In addition, as with any plastic, oxygen will, over time penetrate inward through the outer plastic shell of the unit while the device is in its stationary storage phase. Such a minute increase in oxygen concentration would also affect the density of the coolant mixture being circulated by the micro-motor through the air flow chamber. Therefore, since even a small increase in the oxygen content could cause the micro-motor to increase its optimum number of revolutions per minute (rpms), the aforementioned oxygen sensor with its readout means is programmed to alert technicians to admit additional inert gas through the proper injection port, or alternatively, the sensor may automatically trigger the pneumatic burst thus eliminating a proportionate amount of unwanted oxygen through the oxygen port. The plastic employed will not readily allow such oxygen permeation, but since the unit may be used to store blood and other living biological matter for indefinite periods of time, such provisions for oxygen permeations are anticipated in the design.

In one preferred embodiment, the starch derivative (HES) is added in situ in the presence of the material to be preserved. If gelling is desired, a gelling agent, i.e., of the acrylamide type may be used. As stated in my earlier U.S. Pat. No. 4,473,552, biological matter containing living cells has been incorporated in the HES, at preferably 38° F., for an indefinite period.

The storage container disclosed herein allows the swelling, gelation and storage of the living biological matter in a solution to be conducted in an environment devoid of oxygen, since all air is excluded from the container well. In such an environment, the biological matter stored therein may be maintained for an indefinite period of time.

DETAILED DESCRIPTION OF THE INVENTION

Figure 1:
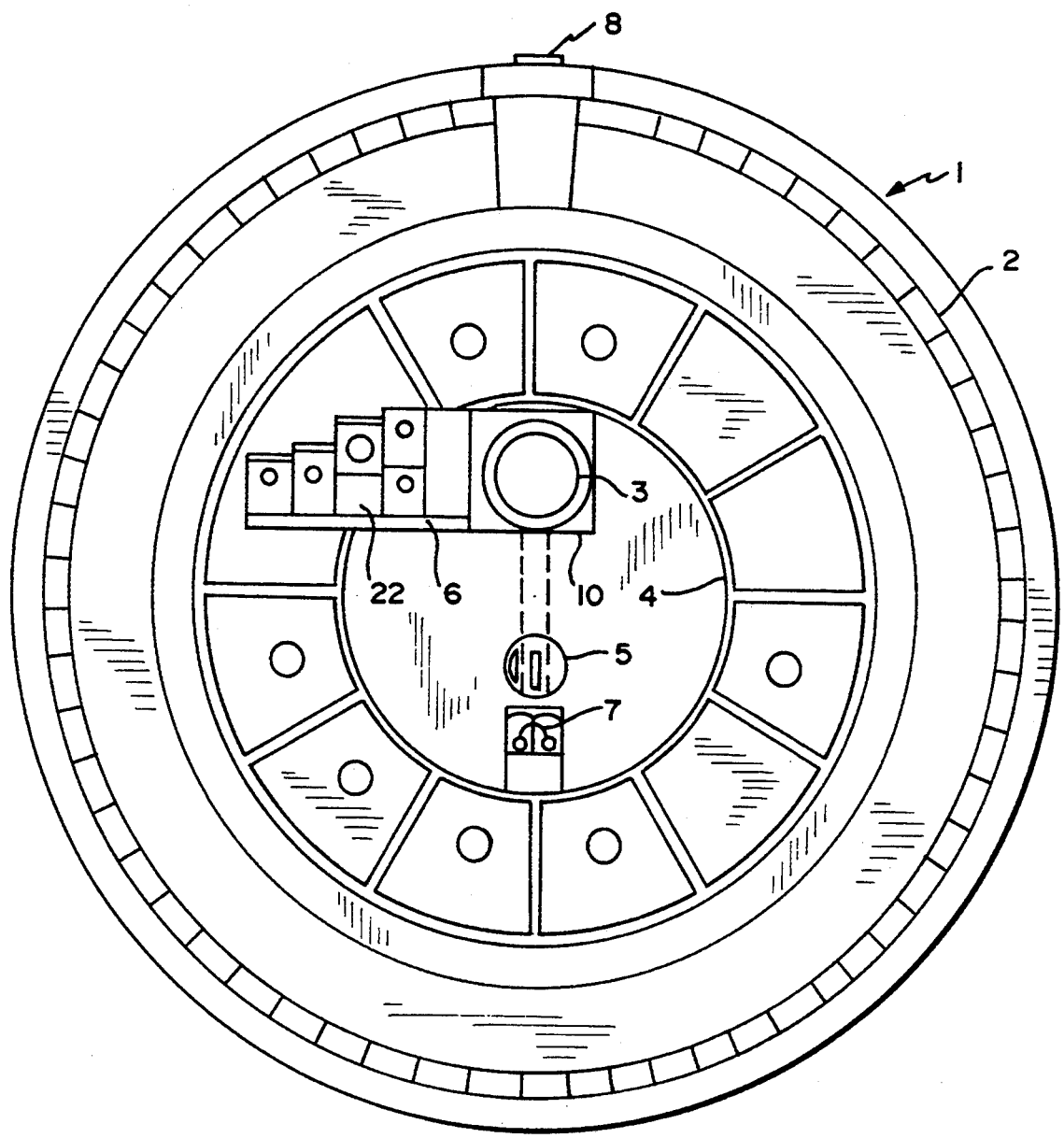
FIG. 1 is a top view of the preservation container.

A transportable closed-system two piece biological matter preservation and support system 1 constructed of polyethylene, polypropylene, polyurethane or other inert plastic, etc. is shown in FIG. 1 from an overhead view, wherein a cover upper portion 2 consists of a micro-motor assembly 3 visible within the transparent lucite shield 4. A fiberscoptic meter readout 5 displays the oxygen content in the empty airflow chamber (FIG. 3) which is sensed by an oxygen sensor 6 (see FIG. 1 for fiberscoptic meter readout 5 and oxygen sensor 6). Since no additional oxygen is allowed into the system, the only oxygen present in the system is in the biological matter being preserved. A suitable readout means for a weight sensor (not shown) is also contemplated for the purpose of monitoring the weight of the biological contents being preserved. The weight of the contained biological matter should remain constant if biodegradation has ceased. The removable upper portion 2 also has twin insertion ports 7 for introduction of suitable inert gas refrigerant or compressed air either hypodermically, or through a larger introduction means (not shown). The refrigerant may be nitrogen, freon, helium, or other inert gas. External circumferential threading secures together the two portions of the container. A stainless steel retaining rim (not shown) surrounds a structural lip 8 from both the upper and lower portions of the container with a pressure lock. A transparent lucite shield 4 is molded into the upper portion of the container and the rechargeable battery pack 10 which powers the instrumentation with digital readout 22, is located on the underside of the upper portion 2.

Figure 2:
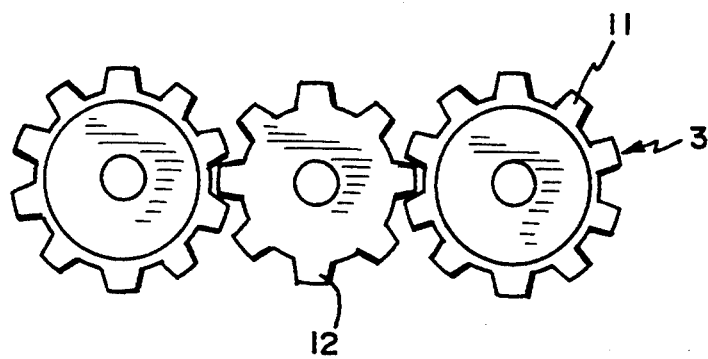
FIG. 2 is a perspective view of the micro-motor unit.

FIG. 2 shows the micro motor assembly 3 in greater detail. The micro-motor 3 is made with low-friction, low-mass compounds, such as silicon, which facilitates the capability for achieving extremely high and sustained revolutions per minute (rpm) with a minimum of pneumatic force applied to the gears 11 of the motor 3. The teeth 12 of the gears 11 are also clearly shown. The inert gas introduced to the system through the injection ports 7 has its airflow path directed to the micro-motor assembly 3 via pneumatic pressure supplied initially which sets the motor 3 into nearly frictionless, virtually "self-sustaining" motion known to range up to 24,000 rpms from a single pneumatic blast of air directed to the motor 3 via a hypodermic syringe (not shown) into the injection ports 7. The micro motor, now in motion, is designed to direct the airflow away from the motor 3 and therefore continually circulate the air, or inert gas mixture around the empty air flow chamber 13 shown in FIG. 3 which surrounds the well 9 containing the biological matter to be preserved at a preferred temperature of 37°–34° F.

Figure 3:
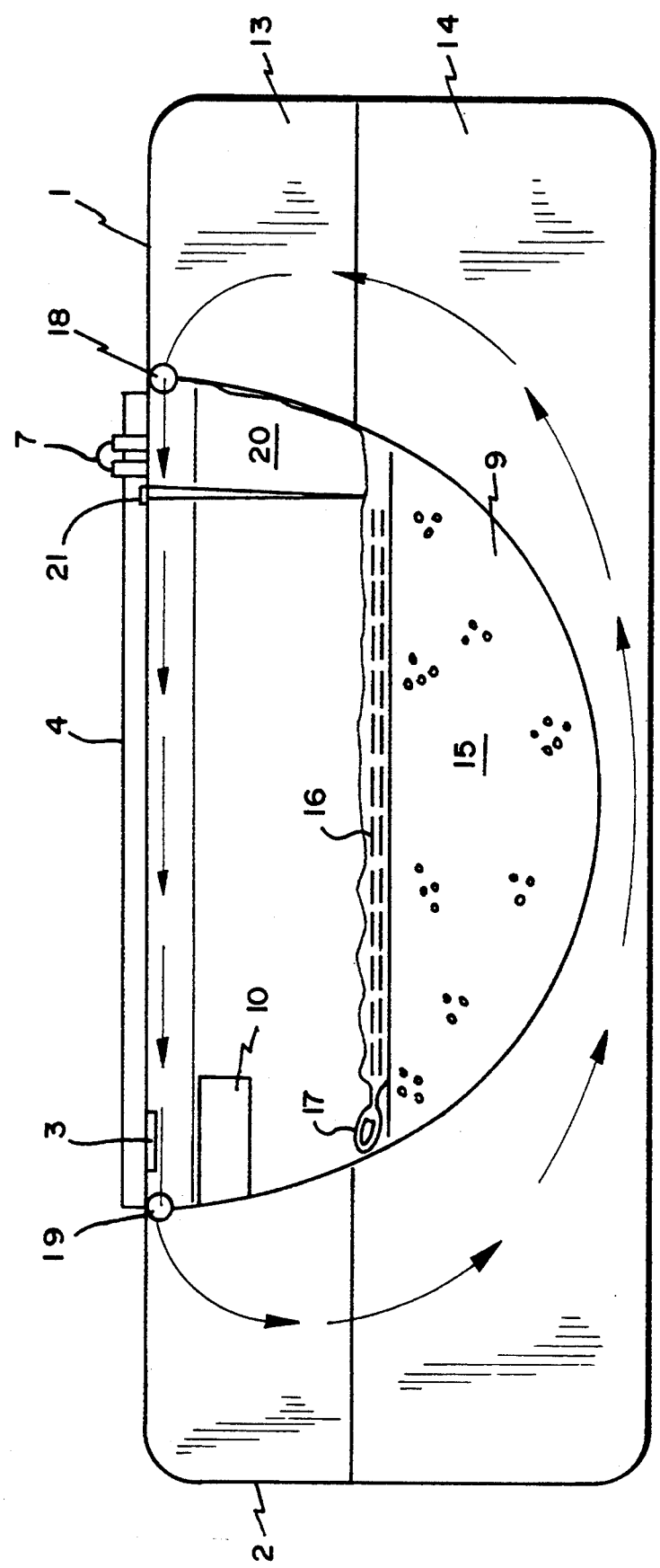
FIG. 3 is a cross-sectional side view of the preservation container showing air flow direction and the storage well.

FIG. 3 shows a cross-sectional side view of the polyethylene, polypropylene, polyurethane, or other inert plastic biological container 1. The lower portion 14 contains a molded concave receptacle, well or chamber 9 comprised of a holding system containing a sterile preservation enhancing medium solution or gelling solution 15 into which is placed the organ or other living biological matter (not shown) sought to be preserved. The preservation-enhancing medium may be an hydroxyethyl starch solution (HES), or a suitable extracellular blocking agent, such as an amantadine or a suitable gel-acrylamide. It is contemplated that a segment of thymus tissue may be stitched to the biological matter being preserved to assist in the tissue's acceptance in the recipient's body. The well 9 is covered by a resealable plastic lid 16 which can be unfastened and pulled back by its tab 17 to accommodate insertion of the biological matter. The lid 16 may then be returned to a sealed configuration by locking into place. A solid latex or other inert plastic structure 20 extends down and rests directly upon the lid of the concave receptacle well which contains the biological matter being preserved. A temperature sensitive means 21 extends down through the solid latex portion of the upper portion of the device and contacts the plastic lid 16 that covers the well 9. The temperature means 21 attached to a suitable readout means, gives an accurate continuous temperature readout of the contents of the well.

The area located between the inside of the concave well 9 and the outer plastic shell of the lower portion 14 and upper portion 2 is comprised of an inert plastic material. In the transportable phase, a refrigerant such as freon would be inserted in the empty airflow chamber and circulated via the micro-motor. When the unit is prepared for stationary storage of the biological contents, the freon may be removed and replaced with other inert gases such as nitrogen, demagnetized helium, etc. The airflow maintains a directional path under the well, up through an air tunnel opening 18 at the top of the upper portion of the unit 2, across the top of the well 9, through the micro-motor 3 and into the said air tunnel opening 19 at the opposite end and again around the concave well 9. The airflow must pass the micro-motor 3 and, is then forceably directed back through the indicated airflow cycle in a unidirectional fashion.

Figure 4:
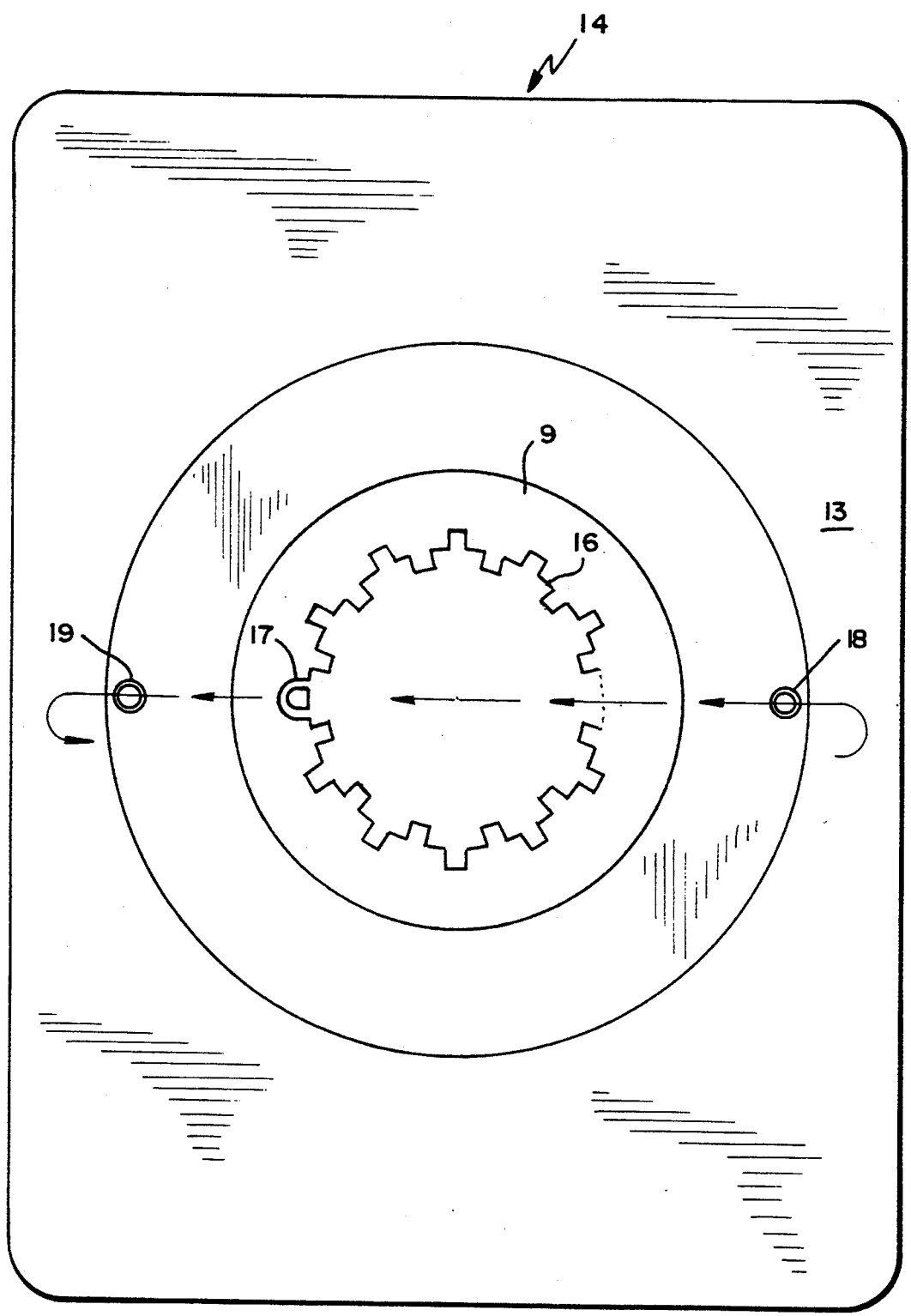
FIG. 4 is a top view of the lower portion of the preservation container with the upper latex portion removed.

FIG. 4 depicts a longitudinal overhead view of the lower portion 14 of the storage unit showing the biological container well 9. It is contemplated that the lower portion 14 of the containing unit which holds the living biological matter will be disposed of after the biological matter contained within has been removed and is either transplanted or otherwise placed into a recipient. However, it is further contemplated that the upper portion 2 of the unit, which contains all instrumentation, the micro-motor 3 and battery pack 10 will be reuseable. Once the biological contents of the lower portion are removed from the storage well 9 and used, the entire lower portion of the device may be discarded. The ability to reuse the upper portion of the device is cost efficient and also conserves space which would be important on long distance space travel where payload and other available cargo space are significant factors that must be considered.

The ability to slow the natural metabolism of living human biological matter through chilling in a proper medium to a temperature above the freezing point causes the biological deterioration of the living tissue, blood, organ or other group of living cells to stop. It is therefore contemplated that indefinite storage and transport of various biological matter will serve to facilitate numerous medical procedures at great distances from suitable donors, and storage will be viable for future space travel, as the containers may be stored for long periods on space stations.

It is further contemplated that as human blood supplies which are known to be healthy and free from unwanted factors, such as the HIV I-II and Hepatitus viruses, fall into shorter supply, the invention will serve to store the healthy blood indefinitely, thus reducing the risk of relying on blood transfusions from an ever depleting supply. A derivative of the white blood cells such as the amantadine molecule, could be added to an HES or gelled preserving medium to any undetected HIV virus, by forming a barrier to prevent HIV penetration of healthy cells and would thus allow acceptability of biological matter in the preserving medium.

While the present invention has been described with respect to its various and preferred embodiments, it is not intended to limit such invention by the description given. Various alternative ways of proceeding and various embodiments, not specifically described, will be readily apparent to those skilled in the art, and it is intended that they be embraced within the scope of the invention, insofar as the appended claims may permit.

What is claimed is:

1. A transportable two part closed-system container for preservation of living biological matter, comprising:

a lower base means having an enclosed sealable concave receptacle means that is sealable with a lid means that provides a gas tight seal for said receptacle means for preservation of living biological matter, and said lower base means also including a first airflow chamber; and a cover means including a second air flow chamber that connects with said first airflow chamber in said base means when said cover means is positioned on said lower base means to permit continuous recirculated flow of refrigerant means immediately adjacent said receptacle means and said lid means, said refrigerant means selected from the group of gases consisting of air and inert gases but said refrigerant means does not contact said living biological matter, said cover means having at least one insertion port means for introduction of said refrigerant means into said connected first and second airflow chambers;

wherein continuous recirculated flow of said refrigerant means, introduced into said connected first and second airflow chambers under pneumatic power, is sustained by a pressure powered micro-motor to maintain viability of said living biological matter at a temperature from about 37° F. to about 34° F.

2. A closed-system container according to claim 1 wherein the living biological matter to be preserved is any living human biological tissue.

3. A closed-system container according to claim 1 wherein said living biological matter to be preserved is human whole blood or blood components, and the viability is preserved for at least 60 days.

4. A closed-system container according to claim 1 wherein the refrigerant means is injected into said connected first and second airflow chambers via built-in injection ports.

5. A closed-system container according to claim 1 further comprising a fiberscoptic meter readout which displays oxygen concentration present in said connected first and second airflow chambers.

6. A closed-system container according to claim 1 wherein the refrigerant means is selected from the group consisting of nitrogen, freon, helium and other inert gases.

7. A closed-system container according to claim 1 wherein said concave receptacle means is comprised of an inert plastic material.

8. A closed-system container according to claim 7 wherein said inert plastic material is selected from the group consisting of polyethylene, polypropylene and polyurethane.

9. A closed-system container according to claim 1 wherein said concave receptacle means is filled with a preservation-enhancing medium selected from the group consisting of hydroexyethyl starch, amantadine and gel acrylamide.

10. A closed-system container according to claim 1 wherein said base means construction is comprised of an inert plastic material.

11. A closed-system container according to claim 10 wherein said plastic material is selected from the group consisting of polyethylene, polypropylene and polyurethane.

12. A closed-system container according to claim 1 wherein said cover means and said lower base means are fastened together via external circumferential threading and a stainless steel rim with a pressure lock.

13. A closed-system container according to claim 1 wherein said micro-motor is comprised of a low friction, low mass material.

14. A closed-system container according to claim 13 wherein said low friction, low mass material is silicon.

15. A closed-system container according to claim 1 further comprising a self-contained rechargeable battery pack which is able to maintain all instrumentation functions with a digital readout.

16. A closed-system container according to claim 1 further comprising an oxygen sensor to monitor oxygen levels within said connected first and second airflow chambers.

17. A process for preserving biological matter having living mammalian cells in a state suitable for transfusion, transplantation or implantation at a temperature from about 37° F. to about 34° F. which comprises the steps of:

removing biological matter from a donor and placing said biological matter into a sealable concave receptacle means inside a sealable transportable two part container having a lower base means including said sealable concave receptacle means;

filling said sealable receptacle means with a preservation-enhancing medium means selected from the group consisting of hydroxyethyl starch solution (HES), an extracellular blocking agent, an amantadine, or a gelacrylamide;

sealing said receptacle means with a resealable plastic lid means that provides a gas tight seal for said receptacle means;

placing a cover means including a first airflow chamber over said lower base means to form said sealable container and to connect said first airflow chamber to a second airflow chamber in said lower base means so as to have said connected first and second airflow chambers in such a relationship as to permit flow of gases immediately adjacent to said sealable concave receptacle means and said plastic lid means but not to permit flow of gases into or out of said sealable concave receptacle means which has been sealed by said lid means;

inserting refrigerant means selected from the group consisting of air and inert gases into said connected first and second airflow chambers under sufficient pressure to power an integrated micro-motor, the insertion of said refrigerant means into said connected first and second airflow chambers being made through at least one hypodermic port means provided on the exterior of said cover means;

circulating said refrigerant means through said first and second air flow chambers via said micro-motor to maintain storage temperatures within said sealable concave receptacle means from about 37° F. to about 34° F.

18. The process of claim 17 wherein said living biological matter comprises living human biological tissue.

19. The process of claim 17 wherein said living biological matter comprises human whole blood.

20. The process of claim 17 wherein said preservation-enhancing medium means is selected from the group consisting of hydroxyethyl starch, amantadine and gel acrylamide.

* * * * *